United States Patent [19]

Rosenberg et al.

[11] Patent Number: 4,692,149
[45] Date of Patent: Sep. 8, 1987

[54] CATHETER WITH REMOVABLE CONNECTOR

[75] Inventors: Helmut W. G. Rosenberg, McHenry, Ill.; George W. Drach, Tucson, Ariz.

[73] Assignee: The Kendall Company, Boston, Mass.

[21] Appl. No.: 895,770

[22] Filed: Aug. 12, 1986

Related U.S. Application Data

[63] Continuation of Ser. No. 683,055, Dec. 18, 1984, abandoned.

[51] Int. Cl.⁴ .............................................. A61M 29/00
[52] U.S. Cl. ........................................ 604/99; 604/49
[58] Field of Search ........................ 604/283, 99–103, 604/49, 50, 51, 52, 53, 54

[56] References Cited

U.S. PATENT DOCUMENTS

| | | | |
|---|---|---|---|
| 3,385,301 | 5/1968 | Harautuneian | 604/99 |
| 3,513,849 | 5/1970 | Vaillancourt et al. | 604/99 X |
| 3,805,794 | 4/1974 | Schlesinger | 604/99 |
| 3,825,013 | 7/1974 | Craven | 604/99 |
| 3,961,632 | 6/1976 | Moossun | 604/50 X |
| 4,198,984 | 4/1980 | Taylor | 604/99 |
| 4,356,824 | 11/1982 | Vazquez | 604/98 |
| 4,429,856 | 2/1984 | Jackson | 604/99 X |

Primary Examiner—John D. Yasko
Attorney, Agent, or Firm—Powell L. Sprunger

[57] ABSTRACT

A catheter comprising, an elongated shaft having a drainage lumen extending through the shaft, and a hollow connector removably connected to a proximal end of the shaft.

6 Claims, 8 Drawing Figures

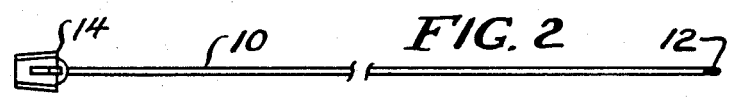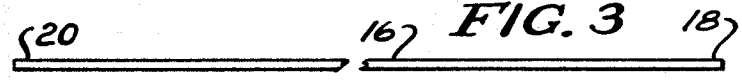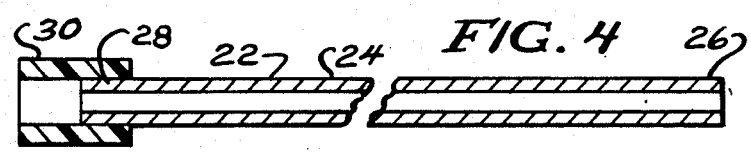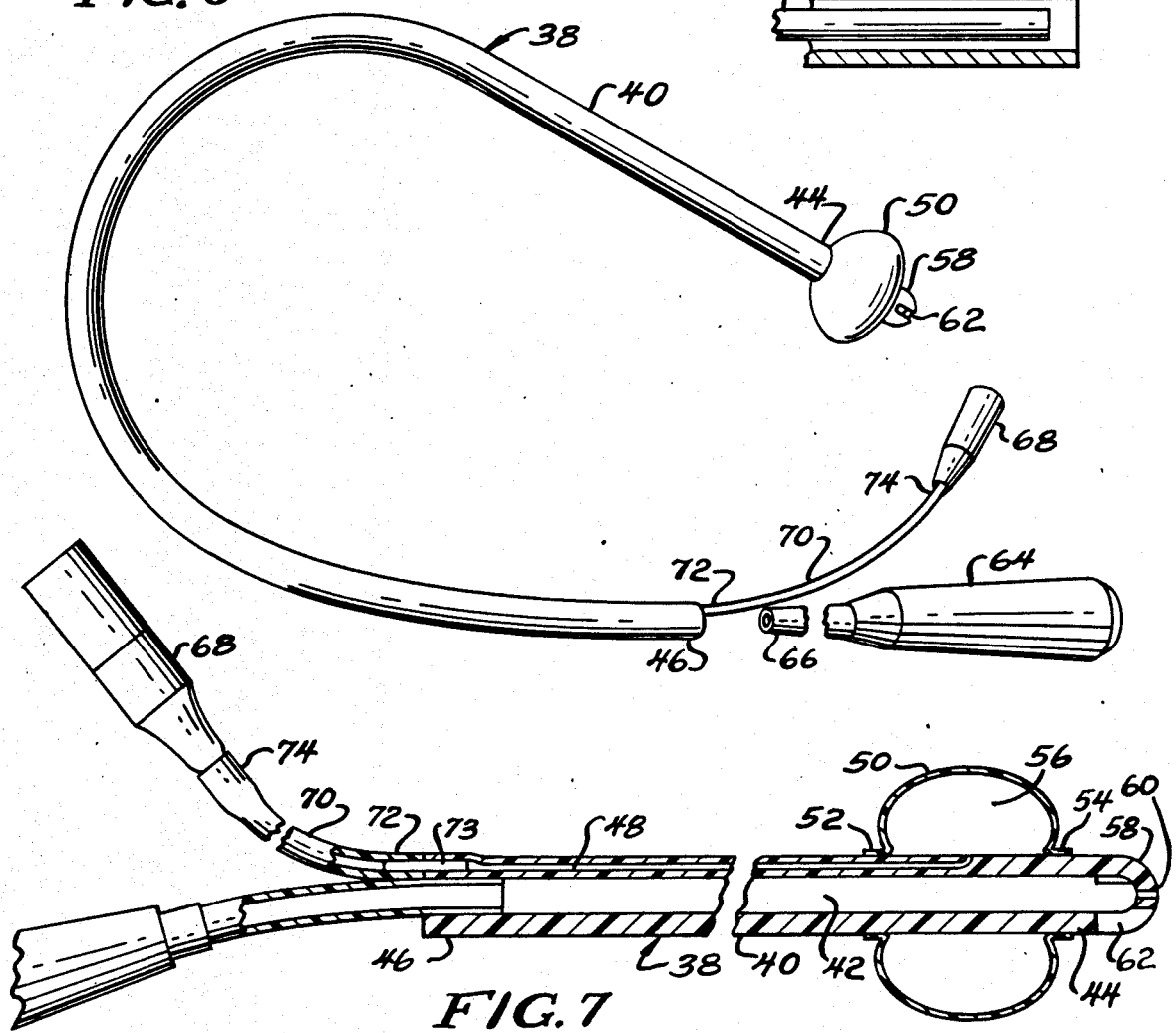

CATHETER WITH REMOVABLE CONNECTOR

This is a continuation of application Ser. No. 683,055, filed Dec. 18, 1984 now abandoned.

BACKGROUND OF THE INVENTION

The present invention relates to catheters.

When the ureter or kidney of a patient is obstructed by a stone, it is necessary to stabilize the kidney through drainage because an increase of pressure in the kidney could result in loss of the kidney. Such a procedure is called a nephrostomy procedure. First, a small gauge hollow needle is passed under radiologic vision until a tip of the needle is located in the renal calyces to obtain access to the kidney chamber. With the needle in place, a flexible elongated guide wire is passed through the needle, and the needle is removed with the guide wire in place to establish a path to the kidney. Next, a plurality of dilators are inserted over the guide wire in order to increase the size of the path to the kidney, and the dilators are then removed. In the past, a catheter is then placed over the guide wire, with the catheter having a pig tail which is located in the kidney. Although nephrostomy has been completed in this manner, it is desired to improve the procedure.

SUMMARY OF THE INVENTION

A principal feature of the present invention is the provision of an improved catheter for performing a nephrostomy procedure.

The catheter of the present invention comprises, an elongated shaft having a drainage lumen extending through the shaft, and a hollow connector.

A feature of the present invention is that the connector is removably connected to a proximal end of the shaft.

Another feature of the present invention is that the catheter has an inflation valve of relatively small diameter located proximal the connector.

Yet another feature of the present invention is that the connector may be removed from the shaft, and a scope sheath may be passed over the catheter and valve.

A further feature of the invention is the provision of a method of performing a nephrostomy procedure.

Further features will become more fully apparent in the following description of the embodiments of this invention and from the appended claims.

DESCRIPTION OF THE DRAWINGS

In the drawings:

FIG. 1 is a diagrammatic view of a kidney of a patient;

FIG. 2 is a fragmentary elevational view of a needle for performing a nephrostomy procedure;

FIG. 3 is a fragmentary elevational view of a guide wire for performing the procedure;

FIG. 4 is a fragmentary elevational view of a stylet for performing the procedure;

FIG. 5 is a fragmentary elevational view of a scope for use in the procedure;

FIG. 6 is a perspective view of a catheter for performing the nephrostomy procedure;

FIG. 7 is a fragmentary sectional view of the catheter of FIG. 6,

DESCRIPTION OF THE PREFERRED EMBODIMENTS

Figure 8:
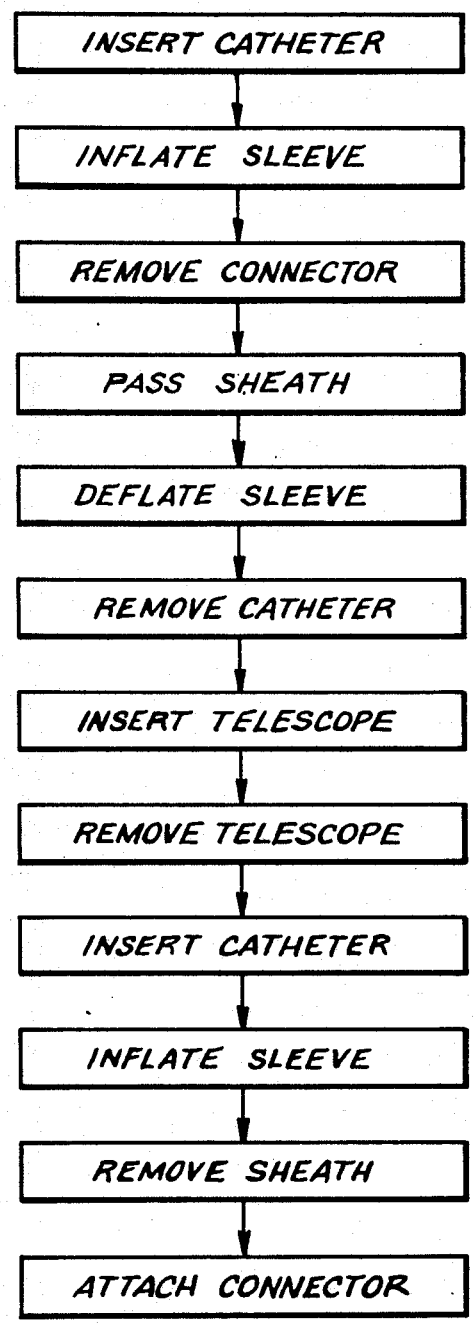
FIG. 8 in a diagrammatic view of methods of the present invention.

A kidney K of a patient having a renal calyces C defining a cavity in the kidney K is shown in FIG. 1. With reference to FIG. 2, a hollow needle 10 is shown having a sharp distal tip 12 and a proximal hub 14. With reference to FIG. 3, a guide wire 16 of flexible material is illustrated having a distal end 18 and a proximal end 20.

A stylet 22 is shown in FIG. 4 having a hollow rigid tube 24. The tube 24 has a distal end 26 and a proximal end 28. As shown, a flexible plastic tubular section 30 is frictionally received on the proximal end 38 of the tube 24.

A scope 32 for use in a nephrostomy procedure is illustrated in FIG. 5. The scope 32 has an elongated outer hollow sheath 34, and an inner optic telescope 36 removably received in the sheath 34.

A catheter 38 of the present invention is illustrated in FIGS. 6 and 7. The catheter 38 has an elongated elastic shaft 40 having a drainage lumen 42 extending through the shaft 40. The shaft 40 has a distal end 44 and a proximal end 46. The shaft 40 also has an inflation lumen 48 extending through a wall of the shaft 40.

As shown, the catheter 38 has an elastic sleeve 50 bonded in circumferential zones 52 and 54 to a distal portion of the shaft 40, such that the sleeve 50 defines a cavity 56 beneath the sleeve 50 communicating with the inflation lumen 48.

The catheter 38 has a distal tip 58 bonded to the distal end 44 of the shaft 40. The tip has a distal opening 60 extending through the tip 58 and communicating with the drainage lumen 42 for a purpose which will be described below. The tip 58 also has a plurality of drainage eyes 62 extending through the tip 58 and communicating with the drainage lumen 42.

As shown, the catheter 38 has a hollow proximal connector 64 removably connected to the proximal end 46 of the shaft 40. In a preferred form, a distal end 66 of the connector 64 is received in a proximal portion of the drainage lumen 42, with the distal end 66 frictionally engaging against the inner wall of the shaft 40 to releasably retain the connector 64 in place. In this configuration, the connector 64 defines a continuation of the drainage lumen 42.

The catheter 38 has an inflation valve 68 of relatively small diamater, such as less then the diameter of the shaft 40, with the valve 68 being of known type which actuates responsive to contact by the tip of a syringe. The valve 68 is connected to the shaft 40 by a hollow tubular section 70 with a distal end 72 of the tubular section 70 being connected by a hollow tubular section 73 to the inflation lumen 48, and a proximal end 74 is connected to the valve 68, such that the tubular section 70 establishes communicaiton between the valve 68 and the inflation lumen 48. As shown, in a preferred form, the valve 68 is located proximal the attached connector 64.

In use, the needle 10 is passed through the body of a patient under radiologic vision until the tip 12 of the needle 10 is located in the renal calyces C to obtain access to the kidney chamber. With the needle 10 in place, the guide wire 16 is passed through the needle 10, and the needle is removed with the guide wire in place to establish a path to the kidney K. Next, a plurality of dilators are inserted over the guide wire in order to increase the size of the path to the kidney, and the dilators are then removed.

The stylet 22 is then inserted through the connector 64 into the drainage lumen 42, until the distal end 26 of the stylet 22 contacts the tip 58. Next, the guide wire 16 is passed through the opening 60 and through the stylet 22, and the catheter 38 is advanced over the guide wire 16 with the stylet 22 supplying rigidity to the catheter 38 for the insertion procedure until a distal end of the catheter 38 is located in the renal calyces. The sleeve 50 of the cathter 38 is then inflated in the renal calyces C through use of the syringe to contact and actuate the valve 68 and pump a suitable fluid through the valve 68 and inflation lumen 48 into the cavity 56 to inflate the sleeve 50. After inflation of the sleeve 50, the stylet 22 is removed from the catheter 38. Finally, the connector 64 is attached to the upstream portion of a drainage tube connected to a drainage bag, and urine drains through the drainage lumen 42 and drainage tube into the drainage bag for collection therein.

In the event that the physician would desire to view the inside of the kidney, the scope 32 is used in the procedure. First, the connector 64 is removed from the shaft 40, and the sheath 34 is advanced over the valve 68 and over the catheter shaft 40. Next, the sleeve 50 is deflated using a syringe, and the catheter 38 is removed through the sheath 34, after which the optic telesope 36 is inserted through the sheath 34 to view the inside of the kidney K. In accordance with the present invention, the catheter 38 facilitates insertion of the sheath 34 of the scope 32, and it is not necessary to redefine the tract to the kidney K.

When viewing of the kidney by the scope 32 is completed, the telescope 36 is removed from the sheath 34, and the catheter 38 is inserted through the sheath 34 until the distal portion of the catheter 38 is located in the renal calyces. Next, the sheath 34 is removed over the catheter shaft 40 and valve 68 with the connector 64 removed from the shaft 40. After removal of the sheath 34, the connector 64 is again attached to the shaft 40, the sleeve 50 is inflated in the renal calyces, and the drainage tube is attached to the connector 64 for continued drainage of the kidney K.

According to a method of performing the nephrostomy procedure of the present invention, a catheter is inserted into a patient's body until a distal portion of the catheter is located in the renal calyces, a sleeve of the catheter is inflated in the renal calyces, a proximal connector of the catheter is removed, and a sheath of a scope is inserted over an inflation valve of the catheter and over the catheter.

The foregoing detailed description is given for clearness of understanding only, and no unnecessary limitations should be understood therefrom, as modifications will be obvious to those skilled in the art.

I claim:

1. A nephrostomy catheter, comprising:
    an elongated shaft having a drainage lumen extending through the shaft, wherein the shaft includes an inflation lumen extending along the shaft, the catheter includes an elastic sleeve bonded in circumferential zones to a distal portion of the shaft, and an inflation valve of relatively small diameter permanently attached to the shaft and communicating with the inflation lumen;
    said catheter having a hollow connector removably connected to a proximal end of the shaft
    an adapter removably received in the connector; and
    a drainage tube fixedly attached to the adapter.

2. The catheter of claim 1 wherein a distal end of the connector is removably received in a proximal end of the drainge lumen.

3. The catheter of claim 1 wherein the valve is located proximal the connector.

4. The catheter of claim 4 including a hollow tubular section communication between the inflation lumen and valve.

5. A method of performing a nephrostomy procedure with a catheter having a distal inflatable sleeve, a proximal removable connector, and a proximal inflation valve, and with a scope having a sheath and a telescope, comprising the steps of:
    inserting a catheter into a patient's body until a distal portion of the catheter is located in the renal calyces;
    inflating a sleeve of the catheter in the renal calyces;
    removing a proximal connector of the catheter;
    passing a sheath of a scope over an inflation valve of the catheter and the catheter while the catheter maintains a path to the kidney;
    deflating the sleeve;
    removing the catheter; and
    inserting a telescope through the sheath.

6. The method of claim 5 including the steps of removing the telescope from the sheath, inserting the catheter through the sheath, inflating the sleeve in the renal calyces, removing the sheath over the catheter and valve, and attaching the connector to the catheter.

* * * * *